United States Patent
Alitalo et al.

(10) Patent No.: US 7,420,042 B2
(45) Date of Patent: Sep. 2, 2008

(54) SOLUBLE NEUROPILIN/GROWTH FACTOR RECEPTOR FUSION PROTEINS

(75) Inventors: Kari Alitalo, Helsinki (FI); Ulf Eriksson, Stockholm (SE); Brigitta Olofsson, San Francisco, CA (US); Taija Makinen, Helsinki (FI)

(73) Assignee: Vegenics Limited, Victoria (AU)

( * ) Notice: Subject to any disclaimer, the term of this patent is extended or adjusted under 35 U.S.C. 154(b) by 841 days.

(21) Appl. No.: 10/303,786

(22) Filed: Nov. 26, 2002

(65) Prior Publication Data

US 2003/0125523 A1    Jul. 3, 2003

Related U.S. Application Data

(62) Division of application No. 09/421,365, filed on Oct. 19, 1999, now Pat. No. 6,515,105.

(60) Provisional application No. 60/112,991, filed on Dec. 18, 1998, provisional application No. 60/104,723, filed on Oct. 19, 1998.

(51) Int. Cl.
*C12P 21/08* (2006.01)
*C07K 14/71* (2006.01)
(52) U.S. Cl. .................... 530/387.3; 530/359; 530/399
(58) Field of Classification Search .................. None
See application file for complete search history.

(56) References Cited

OTHER PUBLICATIONS

Park et al., Journal of Biological Chemistry, 269(41):25646-25654, Oct. 1994.*
Olofsson et al., Journal of Biological Chemistry, 271(32):19310-19317, Aug. 1996.*
Charnow et al. Tibtech, 14:52-60, 1996.*
Roush, "Receptor Links Blood Vessels, Axons", Science 279:2042 (1998).
Migdal et al., "Neuropilin-1 Is a Placenta Growth Factor-2 Receptor", The Journal of Biological Chemistry, 273:22272-22278 (1998).
Neuropilin-1 Is Expressed by Endothelial and Tumor Cells as an Isoform Specific Receptor for Vascular Endothelial Growth Factor, by Shay Soker, et al., Cell vol. 92, 735-745, Mar. 20, 1998.
Tanja Veikkola, et al., "VEGF's Receptors and Angiogenesis", Seminars in Cancer Biology, Jun. 1999, pp. 211-220, vol. 9, No. 1998. 0091, Academic Press, XP-002198307.
Marc G. Achen, et al., "Vascular Endothelial Growth Factor D (VEGF-D) is a Ligand for the Tyrosine Kinases VEGF Receptor 2 (Flk1) and VEGF Receptor 3 (Flt4)", Proc. Natl. Acad. Sci., Jan. 1998, pp. 548-553, vol. 95, XP002905751.
Taija Makinen, et al., "Differential Binding of Vascular Endothelial Growth Factor B Splice and Proteolytic Isoforms to Neuropilin-1", The Journal of Biological Chemistry, Jul. 23, 1999, pp. 21217-21222, vol. 274, No. 30, The American Society for Biochemistry and Molecular Biology, Inc., XP002944607.

* cited by examiner

*Primary Examiner*—Marianne P Allen
(74) *Attorney, Agent, or Firm*—Marshall, Gerstein & Borun LLP

(57) ABSTRACT

Complexes of a protein selected from the group consisting of $VEGF-B_{167}$, VEGF-C, VEGF-D and processed $VEGF-B_{186}$ and analogs thereof and the neuropilin-1 (NP-1) receptor, the extracellular domain or a ligand-binding fragment or analogue thereof; the use of such complexes in assays for growth factor proteins having substantially the same binding affinity for a cell surface receptor as $VEGF-B_{167}$, VEGF-C, VEGF-D or processed $VEGF-B_{186}$ and/or in promoting or antagonizing a cellular response mediated by $VEGF-B_{167}$, VEGF-C, VEGF-D and/or processed $VEGF-B_{186}$; and specific binding partners, e.g. antibodies, for such complexes.

5 Claims, 8 Drawing Sheets

SOLUBLE NEUROPILIN/GROWTH FACTOR RECEPTOR FUSION PROTEINS

CROSS REFERENCE TO RELATED APPLICATIONS

This application is a division of application Ser. No. 09/421,365, filed Oct. 19, 1999, and now U.S. Pat. No. 6,515,105.

This application claims the benefit of U.S. Provisional Application No. 60/104,723, filed Oct. 19, 1998; and U.S. Provisional Application No. 60/112,991, filed Dec. 18, 1998.

FIELD OF THE INVENTION

The present invention relates to complexes of the Neuropilin-1 (NP-1) receptor and a growth factor selected from the group consisting of Vascular Endothelial Growth Factor-$B_{167}$ (VEGF-$B_{167}$), Vascular Endothelial Growth Factor-C (VEGF-C), Vascular Endothelial Growth Factor-D (VEGF-D) and the processed form of Vascular Endothelial Growth Factor-$B_{186}$ (processed VEGF-$B_{186}$), to methods of using such complexes to induce or antagonize a cellular response mediated by one or more of said growth factors, and to isolated binding partners, such as antibodies, which bind to complexes of one or more of the growth factors with NP-1.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., Enzyme & Protein, 1996 49 138-162; Breier et al., Dev. Dyn. 1995 204 228-239; Risau, Nature, 1997 386 671-674). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation. The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., J. Biol. Chem., 1992 267 10931-10934 for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF family, and appear to act primarily via endothelial receptor tyrosine kinases (RTKs).

Nine different proteins have been identified in the PDGF family, namely two PDGFs (A and B), VEGF and six members that are closely related to VEGF. The six members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C, described in Joukov et al., EMBO J., 1996 15 290-298 and Lee et al., Proc. Natl. Acad. Sci. USA, 1996 93 1988-1992; VEGF-D, described in International Patent Application No. PCT/US97/14696 (WO 98/07832), and Achen et al., Proc. Natl. Acad. Sci. USA, 1998 95 548-553; the placenta growth factor (PlGF), described in Maglione et al., Proc. Natl. Acad. Sci. USA, 1991 88 9267-9271; VEGF2, described in International Patent Application No. PCT/US94/05291 (WO 95/24473) by Human Genome Sciences, Inc; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., Nature, 1996 380 435-439; Ferrara et al., Nature, 1996 380 439-442; reviewed in Ferrara and Davis-Smyth, Endocrine Rev., 1997 18 4-25). The significance of the role played by VEGF has been demonstrated in studies showing that inactivation of a single VEGF allele results in embryonic lethality due to failed development of the vasculature (Carmeliet et al., Nature, 1996 380 435-439; Ferrara et al., Nature, 1996 380 439-442). In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara et al., J. Cellular Biochem., 1991 47 211-218 and Connolly, J. Cellular Biochem., 1991 47 219-223. Alterative mRNA splicing of a single VEGF gene gives rise to five isoforms of VEGF.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences. VEGF-B may potentiate the mitogenic activity of low concentrations of VEGF both in vitro and in vivo.

VEGF-B was isolated using a yeast co-hybrid interaction trap screening technique by screening for cellular proteins which might interact with cellular resinoid acid-binding protein type I (CRABP-I). Its isolation and characteristics are described in detail in PCT/US96/02957 and in Olofsson et al., Proc. Natl. Acad. Sci. USA, 1996 93 2576-2581.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 1996 15 290-298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 1998 95 548-553). Its isolation and characteristics are described in detail in International Patent Application No. PCT/US97/14696 (WO98/07832).

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 1991 88 9267-9271. Presently its biological function is not well understood.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

VEGF3 was isolated from a cDNA library derived from colon tissue. VEGF3 is stated to have about 36% identity and 66% similarity to VEGF. The method of isolation of the gene encoding VEGF3 is unclear and no characterization, of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

VEGF-B exhibits approximately 40 to 45 percent sequence identity to VEGF and approximately 30 percent sequence identity to PlGF. Alternative splicing of PlGF and VEGF-B mRNA's give rise to two protein isoforms, PlGF-1 and PlGF-2 and VEGF-B$_{167}$ and VEGF-B$_{186}$, respectively (Hauser et al., Growth Factors, 9:259 (1993); Maglione et al., Oncogene, 8:925 (1993); Olofsson et al., J. Biol. Chem., 274:19310 (1996)), all of which bind to Flt-1. In both cases, one of these isoforms, PlGF-2 and VEGF-B$_{167}$, has a basic C-terminus that binds to the cell surface heparin sulfate proteoglycans (HSPGs) and can be released by heparin. The heparin binding region resembles the amino acid sequence encoded by exon 7 of the VEGF gene.

VEGF-C and VEGF-D differ from other members of the VEGF family in that they have N- and C-terminal extensions flanking the VEGF-homology domain and are proteolytically processed (Joukov et al., EMBO J., 16:3898 (1997), Achen et al., Proc. Natl. Acad. Sci. USA, 95:548 (1998)). In addition, VEGF-C is not known to bind heparin, whereas VEGF-B$_{167}$ and some forms of VEGF (VEGF$_{165}$, VEGF$_{189}$ and VEGF$_{206}$) do. The mature form of VEGF-D lacks the polybasic region that characterizes VEGF/PlGF heparin-binding domains.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are Flt-1/VEGFR-1 [Shibuya et al., Oncogene, 5:519-524 (1990); de Vries et al., Science, 255:989-991 (1992)]; Flk-1/KDR/VEGFR-2 [Matthews et al., Proc. Natl. Acad. Sci. USA, 88:9026-30 (1991); Terman et al., Biochem. Biophys. Res. Comm., 187:1579-86 (1992); Millauer et al., Cell, 72:835-46 (1993)]; and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., The EMBO Journal, 1996 15 290-298). VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

VEGFR-1, VEGFR-2 and VEGFR-3 are expressed differently by endothelial cells. Both VEGFR-1 and VEGFR-2 are expressed in blood vessel endothelia (Oelrichs et al., Oncogene, 1992 8 11-18; Kaipainen et al., J. Exp. Med., 1993 178 2077-2088; Dumont et al., Dev. Dyn., 1995 203 80-92; Fong et al., Dev. Dyn., 1996 207 1-10) and VEGFR-3 is mostly expressed in the lymphatic endothelium of adult tissues (Kaipainen et al., Proc. Natl. Acad. Sci. USA, 1995 9 3566-3570). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., Nature, 1995 376 66-70) However, deletion of the intracellular tyrosine kinase domain of VEGFR-1 generates viable mice with a normal vasculature (Hiratsuka et al., Proc. Natl. Acad. Sci. USA 1998 95 9349-9354). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., Nature, 1995 376 62-66; Shalaby et al., Cell, 1997 89 981-990). Inactivation of VEGFR-3 results in cardiovascular failure due to abnormal organization of the large vessels (Dumont et al. Science, 1998 282 946-949).

Although VEGFR-1 is mainly expressed in endothelial cells during development, it can also be found in hematopoetic precursor cells during early stages of embryogenesis (Fong et al., Nature, 1995 376 66-70). In adults, monocytes and macrophages also express this receptor (Barleon et al., Blood, 1996 87 3336-3343). In embryos, VEGFR-1 is expressed by most, if not all, vessels (Breier et al., Dev. Dyn., 1995 204 228-239; Fong et al., Dev. Dyn., 1996 207 1-10).

The receptor VEGFR-3 is widely expressed on endothelial cells during early embryonic development but as embryogenesis proceeds becomes restricted to venous endothelium and then to the lymphatic endothelium (Kaipainen et al., Cancer Res., 1994 54 6571-6577; Kaipainen et al., Proc. Natl. Acad. Sci. USA, 1995 92 3566-3570). VEGFR-3 is expressed on lymphatic endothelial cells in adult tissues. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., EMBO J., 1996 15 290-298).

Some inhibitors of the VEGF/VEGF-receptor system have been shown to prevent tumor growth via an anti-angiogenic mechanism; see Kim et al., Nature, 1993 362 841-844 and Saleh et al., Cancer Res., 1996 56 393-401.

Recently, a novel 130-135 kDa VEGF isoform specific receptor has been purified and cloned (Soker et al., Cell, 1998 92 735-745). The VEGF receptor was found to specifically bind the $VEGF_{165}$ isoform via the exon 7 encoded sequence, which shows weak affinity for heparin (Soker et al., Cell, 1998 92 735-745). Surprisingly, the receptor was shown to be identical to human neuropilin-1 (NP-1), a receptor involved in early stage neuromorphogenesis. PlGF-2 also appears, to interact with NP-1 (Migdal et al., J. Biol. Chem., 1998 273 22272-22278). NP-1 expression enhanced the binding of $VEGF_{165}$ to KDR and enhanced the bioactivity of $VEGF_{165}$ (Soker et al., Cell, 92:735-745 (1998)).

NP-1 has been identified as a receptor that mediates chemorepulsant activity of the collapsin/semiphorins (collapsin-1/Sema III/Sema D), a large family of transmembrane and secreted glycoproteins that function in repulsive cone and axon guidance [See Kolodkin et al., Cell, 75:1389-1399 (1993); Zhigang et al., Cell, 90:739-751 (1997); Kolodkin et al., Cell, 90: 753-762 (1997)]. The $K_d$ of Sema III binding to NP-1, $2-3\times10^{-10}$M, is similar to the $K_d$ of $VEGF_{165}$ to NP-1, $2-3\times10^{-10}$M (Zhigang et al., Cell, 90:739-751 (1997); Kolodkin et al., Cell, 90: 753-761; Soker et al., Cell 92:735-745 (1998)). These findings are especially surprising because two structurally different ligands with markedly different biological activities (namely, stimulation of angiogenesis by VEGF and chemorepulsion of neuronal cells by Sema III) bind to the same receptor and with similar affinity.

NP-1 expression is found in some tumor cell lines, and is prominent in some organs where VEGF-B is highly expressed, such as heart, pancreas and skeletal muscle.

SUMMARY OF THE INVENTION

The present invention is based on the discovery that $VEGF-B_{167}$, VEGF-C, VEGF-D and processed $VEGF-B_{186}$ are each capable of binding to the extracellular domain of NP-1 to form bioactive complexes which mediate useful cell responses and/or antagonize undesired biological activities.

According to the present invention, it has been found that $VEGF-B_{167}$ binds to the NP-1 receptor via the exon 6B encoded sequence in the region responsible for heparin binding. Binding also occurs between NP-1 and PlGF-2, VEGF-C, VEGF-D and processed $VEGF-B_{186}$.

VEGF-B exists in various isoforms as a result of alternative splicing. $VEGF-B_{167}$ is composed of exons 1 through 5 plus exon 6B and exon 7, with the stop codon being in exon 7. $VEGF-B_{186}$ is composed of exons 1 through 5 plus exon 6A, and it terminates in exon 6B, albeit in a different reading frame than that used in exon 6B for $VEGF-B_{167}$. Exon 7 is not translated in $VEGF-B_{186}$. As noted, $VEGF-B_{167}$ binds to NP-1. The fact that the product of a construct expressing only exons 1 through 5 (murine $VEGF-B_{kEx1-5}$ as described in PCT/US97/23533, which is incorporated herein by reference) does not bind NP-1 indicates that the binding site is not in any of exons 1 through 5. Similarly, the fact that processed $VEGF-B_{186}$ does not contain the expression product of exon 7 but can still bind NP-1 indicates that the VEGF-B exon 6B encoded region of $VEGF-B_{167}$ binds NP-1.

The processed form of $VEGF-B_{186}$ also can bind NP-1 and yet does not contain exon 6B. Although the location of the cleavage site which creates the processed form of $VEGF-B_{186}$, as opposed to the full length form, is not known, the processed form comprises exons 1-5 and at least part of exon 6A. Thus, there may be a second binding site coded within the part of exon 6A which is expressed in processed $VEGF-B_{186}$.

According to the present invention, it has been found that VEGF-B, VEGF-C, VEGF-D and other ligands are modular in that the domains may be expressed separately from each other and disassociated. On the cell surface, with respect to $VEGF-B_{167}$, one domain binds Flt-1 and another domain binds neuropilin and heparin sulfate. This independent modularity and dissassociability may be exploited for example, by joining co-receptor binding domains.

Also, it has been found that VEGF-C binds with VEGFR-2 and VEGFR-3 and neuropilin receptors. VEGF-CΔNΔC does not bind NP-1 while full length VEFG-C does.

References herein to the amino acid sequence of VEGF-B refer to the sequence for human VEGF-B described in Eriksson et al., published PCT Application No. WO 96/26736 (Genbank database accession no. U52819). References to the amino acid or nucleotide sequences of NP-1 refer to the sequences described by Soker et al., Cell, 92:735-745 (1998), (EMBL database accession no. AF016050). A useful method for assaying endothelial cell proliferation is described in Olofsson et al., Proc. Natl. Acad. Sci. USA, 93:2576-81 (1996).

A sample containing the receptor protein could be, for example, soluble NP-1 receptor produced naturally in the conditioned medium of cells that normally express the receptor. Tissue samples or tissue fluids shed naturally from cells by proteolytic events also could be used as receptor samples.

An analog or functional analog refers to a modified form of the respective polypeptide in which at least one amino acid substitution has been made such that the analog retains substantially the same biological activity as the unmodified polypeptide in vivo and/or in vitro. In addition, analogs of VEGF-B$_{167}$, VEGF-C, VEGF-D or processed VEGF-B$_{186}$ identified by this aspect of the invention may be small molecules, for example proteins or peptides or non-proteinaceous compounds. The analogs also could include VEGF-B$_{167}$, VEGF-C, VEGF-D, processed VEGF-B$_{186}$ or derivatives thereof (including, but not limited to, fragments of monomers or dimers) tagged with a toxin or drug or radioactive isotope which could target NP-1 expressed and upregulated on endothelial cells in tumors. Such molecules could be useful to antagonize or inhibit unwanted cellular responses induced by members of the VEGF family of growth factors, such as tumor-induced angiogenesis or psoriasis or retinopathies by techniques analogous to those described in Kim et al., *Nature*, 362:841-44 (1993) or Aiello et al., *New England Journal of Medicine*, 331:1480-87 (1994).

Abolishing interaction of NP-1 with VEGF-B$_{167}$, VEGF-C, VEGF-D or processed VEGF-B$_{186}$ could alleviate biological activity in cancer. It is also possible that VEGF-B$_{167}$ signals without Flt-1 but via NP-1 by an as yet unknown mechanism in cells. Such signaling may exist in normal and tumor cells which express NP-1. Treatments that inhibit this signaling may be useful in treating cancer and/or in modulation of normal or diseased vasculature.

One procedure for isolating complexes of NP-1 with VEGF-B$_{167}$, VEGF-C, VEGF-D or processed VEGF-B$_{186}$ involves using fusion proteins of the NP-1 receptor, preferably the extracellular domain of NP-1, and immunoglobulin G (IgG) followed by Sepharose A binding. Alternatives to the use of Sepharose A include using ion-exchange chromatography, gel filtration or affinity chromatography. Conditioned medium containing receptor/IgG fusion proteins could be allowed to interact with conditioned medium either from cells either transfected with DNA encoding the respective growth factor ligand or analog thereof, or from cells which naturally express the ligand, or with a solution containing a candidate ligand analog.

Conditioned medium from cultures of cells expressing NP-1-IgG fusion proteins can be passed over a Sepharose A column or matrix to immobilize the receptor, or the fusion proteins can be immobilized in cellulose disks or absorbed onto plastic in the form of an ELISA test. A second solution containing conditioned medium from cells expressing the ligand is then passed over immobilized receptor. If desired, the ligand may be radioactively labeled in order to facilitate measurement of the amount of bound ligand by radioassay techniques.

Such an assay can be used to screen for conditions involving overexpression of the NP-1 receptor, i.e. through detection of increased bound radioactivity compared to a control. This methodology can also be used to screen for the presence of analogs which compete with VEGF-B$_{167}$, VEGF-C, VEGF-D and/or processed VEGF-B$_{186}$, i.e. through detection of decreased bound radioactivity compared to a control indicative of competition between the radioactively labeled ligand used in the test and a non-radioactive putative analog.

Examples of detectable cellular responses to members of the VEGF family include endothelial cell proliferation, angiogenesis, tyrosine phosphorylation of receptors, and cell migration. Isoform specific induction may be accomplished. Specific examples include urokinase-type plasminogen activator (uPA) and plasminogen activator inhibitor type 1 (PAI-1) induction, endothelial cell migration and growth stimulation of some endothelial cell types. Tube formation is also possible.

The cells which express the receptor protein or a portion thereof may be cells which naturally express the receptor, or they may be cells into which the nucleic acid encoding the receptor or a portion thereof is introduced such that the receptor protein or a portion thereof is expressed. Transfection or transduction of nucleic acid encoding neuropilin could be performed to increase expression in cells in vitro and in vivo. Expression in cells not expressing neuropilin, [e.g. hematopoietic cells, see Soker et al., *Cell*, 92:735-745 (1998)] should make them more responsive to induction. Induction should occur by VEGF-B$_{167}$, VEGF-C, VEGF-D or the processed form of VEGF-B$_{186}$, but induction should not occur by the nonprocessed (i.e., full length) form of VEGF-B$_{186}$. Also, expression of NP-1 or a portion thereof by cells adjacent to those expressing a particular RTK could also modulate the effective concentrations of the RTK and/or signaling by the RTK.

Wherever the introduction of a nucleotide sequence encoding NP-1, an extracellular domain thereof, a ligand-binding fragment or analog thereof, or a polypeptide chain having binding affinity for VEGF-B$_{167}$ or VEGF-C and encoded by a nucleic acid that hybridizes under stringent conditions with a nucleic acid encoding the ligand-binding fragment is referred to herein, this may be effected by transformation with a plasmid vector, or transfection either ex vivo or in vivo with a viral vector (e.g., adenoviruses, pox viruses or retroviruses),or with bacterial vectors (e.g., BCG) or by injection of naked DNA.

Heparin may modulate NP-1 binding by those growth factors which bind heparin, and a basic heparin binding peptide could modulate it independent of direct NP-1 interaction. VEGF-C does not bind heparin, so VEGF-C would not be subject to heparin modulation.

Alternatively, the foregoing assay could be reversed by immobilizing the VEGF-B$_{167}$ ligand or candidate analog and contacting the immobilized ligand with conditioned medium from cells expressing the receptor or a portion of the receptor, such as the extracellular domain or the ligand-binding fragment.

Means for detecting protein/receptor binding may comprise, for example, means for detecting specific binding interaction of VEGF-B$_{167}$, VEGF-C, VEGF-D or processed VEGF-B$_{186}$ or an analog of any of them with the NP-1 receptor protein or portion thereof or means for detecting induction of a cellular response induced by VEGF-B$_{167}$, VEGF-C, VEGF-D or processed VEGF-B$_{186}$, such as uPA and PAI-1 induction, and receptor phosphorylation.

A still further aspect of the invention relates to an isolated ligand-receptor complex comprising two molecules, one defining the ligand and comprising the NP-1 binding sequence of VEGF-B$_{167}$, VEGF-C, VEGF-D or processed VEGF-B$_{186}$ (for example, the exon 6B encoded sequence of VEGF-B$_{167}^{186}$) or a receptor-binding analog thereof, and the second defining the receptor and being selected from the group consisting of a polypeptide chain comprising an amino acid sequence of NP-1, the extracellular domain thereof, the ligand-binding domain, a receptor analog of NP-1 which binds VEGF-B$_{167}$, VEGF-C, VEGF-D or processed VEGF-B$_{186}$ and which has at least 90% amino acid identity with the ligand-binding domain, and a polypeptide chain having binding affinity for VEGF-B$_{167}$, VEGF-C, VEGF-D or processed VEGF-B$_{186}$ and encoded by a nucleic acid that hybridizes under stringent conditions with a nucleic acid encoding the ligand-binding fragment. Preferably the receptor is the NP-1 receptor, and the ligand includes the NP-1-binding sequence of VEGF-B$_{167}$, VEGF-C, VEGF-D or processed VEGF-B$_{186}$ (for example, the exon 6B encoded NP-1-binding sequence of VEGF-B$_{167}$).

Isolation and purification of the ligands or complexes could be effected by conventional procedures such as immunoaffinity purification using monoclonal antibodies according to techniques described in standard reference works such as Harlow et al., *Antibodies, a Laboratory Manual*, Cold Spring Harbor Laboratory Press (1988) and/or Marshak et al., *Strategies for Protein Purification and Characterization*, Cold Spring Harbor Laboratory Press (1996). Suitable antibodies to the individual ligands or to the complexes could be generated by conventional techniques.

A cell-free complex could be used either in vivo or in vitro to compete with binding of VEGF-B$_{167}$, VEGF-C, VEGF-D or processed VEGF-B$_{186}$ to a receptor or to prevent dimerization of the cell-bound receptor after ligand binding. Such a cell-free complex would comprise at least one receptor molecule, for example soluble NP-1 (sNP-1), and a dimer molecule. The sNP-1 is defined as a non-membrane bound protein as well as a portion of the receptor, such as the extracellular domain or the ligand-binding fragment of NP-1. The dimer molecule may be a homodimer or mixed dimer of VEGF-B$_{167}$, VEGF-C, VEGF-D or processed VEGF-B$_{186}$ or an analog of any of them. One molecule of the dimer can be bound to the receptor molecule in the complex and the second molecule of the dimer has a free binding site available to bind to a cell surface receptor.

It is also an aspect of the present invention to provide an isolated binding partner having specific binding affinity for an epitope on a ligand-receptor complex comprising VEGF-B$_{167}$, VEGF-C, VEGF-D or processed VEGF-B$_{186}$ protein or an analog thereof in specific binding interaction with the ligand binding domain of a receptor having a polypeptide chain comprising an amino acid sequence of NP-1, the extracellular domain or the ligand-binding domain of NP-1, a receptor analog thereof which binds VEGF-B$_{167}$, VEGF-C, VEGF-D or processed VEGF-B$_{186}$ and which has at least 90% amino acid identity with the ligand-binding domain of NP-1, or a polypeptide chain having binding affinity for VEGF-B$_{167}$, VEGF-C, VEGF-D or processed VEGF-B$_{186}$ and encoded by a nucleic acid that hybridizes under stringent conditions with a nucleic acid encoding the ligand-binding domain of NP-1; wherein the binding partner has substantially no binding affinity for uncomplexed VEGF-B$_{167}$, VEGF-C, VEGF-D or processed VEGF-B$_{186}$ or analog thereof. Exemplary stringent hybridization conditions are as follows: hybridization at 42° C. in 5×SSC, 20 mM NaPO$_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulas for determining such variation exist. See for example Sambrook et al, "Molecular Cloning: A Laboratory Manual", Second Edition, pages 9.47-9.51, Cold Spring Harbor, N.Y.: Cold Spring Harbor Laboratory (1989). Preferably the binding partner also will have substantially no binding affinity for any uncomplexed form of the receptor protein or receptor analog thereof. The binding partner may be an antibody which reacts with or recognizes such growth factor/receptor complexes. Either polyclonal or monoclonal antibodies may be used, but monoclonal antibodies are preferred. Such antibodies can be made by standard techniques, screening out those that bind to either receptor or ligand individually.

As used in this application, percent sequence identity is determined by using the alignment tool of "MEGALIGN" from the Lasergene package (DNASTAR, Ltd. Abacus House, Manor Road, West Ealing, London W130AS United Kingdom) and using its preset conditions. The alignment is then refined manually, and the number of identities are estimated in the regions available for a comparison.

An additional aspect of the invention relates to the use of an antagonist to VEGF-B$_{167}$, VEGF-C, VEGF-D or processed VEGF-B$_{186}$ obtained according to the methods described above for (i) antagonizing binding of VEGF-B$_{167}$, VEGF-C, VEGF-D or processed VEGF-B$_{186}$ to a cell surface receptor, or (ii) antagonizing induction of a cellular response mediated by VEGF-B$_{167}$, VEGF-C, VEGF-D or processed VEGF-B$_{186}$.

A preferred antagonist comprises an antibody having binding specificity for (i) the ligand binding domain of a protein having a polypeptide chain comprising an amino mid sequence of NP-1, an analog thereof which binds VEGF-B$_{167}$, VEGF-C, VEGF-D or processed VEGF-B$_{186}$ and which has at least 90% amino acid identity with the ligand-binding domain of NP-1, or a polypeptide chain having binding affinity for VEGF-B$_{167}$, VEGF-C, VEGF-D or processed VEGF-B$_{186}$ and encoded by a nucleic acid that hybridizes under stringent conditions with a nucleic acid encoding the ligand-binding domain of NP-1; or (ii) a receptor binding domain having a binding affinity for the NP-1 receptor and comprising the NP-1-binding sequence of VEGF-B$_{167}$, VEGF-C, VEGF-D or processed VEGF-B$_{186}$ (for example, the exon 6B encoded NP-1-binding sequence of VEGF-B$_{167}$).

The ligand binding domain of a protein having binding affinity for VEGF-B$_{167}$, VEGF-C, VEGF-D or processed VEGF-B$_{186}$ desirably will exhibit at least 90%, preferably at least 95%, amino acid identity with the ligand-binding domain of NP-1 and especially preferably will correspond thereto. The receptor binding domain of a VEGF-B$_{167}$, VEGF-C, VEGF-D or processed VEGF-B$_{186}$ analog desirably will exhibit at least 90%, preferably at least 95%, sequence identity with the NP-1-binding sequence of VEGF-B$_{167}$, VEGF-C, VEGF-D or processed VEGF-B$_{186}$ (e.g., with the exon 6B encoded NP-1-binding sequence of VEGF-B$_{167}$), and especially preferably will correspond thereto.

Yet another aspect of the invention relates to the use of a protein selected from the group consisting of a polypeptide chain comprising an amino acid sequence of NP-1, the extracellular domain, the ligand-binding domain of NP-1, or an analog thereof which binds VEGF-B$_{167}$, VEGF-C, VEGF-D or processed VEGF-B$_{186}$ and which has at least 90% amino acid identity with the ligand-binding domain of NP-1, and a polypeptide chain having binding affinity for VEGF-B$_{167}$, VEGF-C, VEGF-D or processed VEGF-B$_{186}$ and encoded by a nucleic acid that hybridizes under stringent conditions with a nucleic acid encoding the ligand-binding domain of NP-1; in a method for antagonizing:

(a) binding of VEGF-B$_{167}$, VEGF-C, VEGF-D or processed VEGF-B$_{186}$ to a protein, e.g. a cell surface receptor, or (b) induction of a cellular response mediated by VEGF-B$_{167}$, VEGF-C, VEGF-D or processed VEGF-B$_{186}$.

The polypeptide chain competes with the cell surface receptor for the respective growth factor and ties up the available growth factor, thereby preventing it from effectively interacting with the cell surface receptor and inducing the cellular response normally mediated by that growth factor. A suitable peptide chain could be a solubilized form of the receptor (sNP-1) as described in Soker et al., *Cell*, 92:735-745 (1998).

Additionally, it is an aspect of the invention to provide a method for antagonizing binding of VEGF-B$_{167}$, VEGF-C, VEGF-D or processed VEGF-B$_{186}$ to a cell surface receptor, the method comprising the step of providing a protein having binding specificity for the amino acid sequence of NP-1 or a sequence variant thereof which binds a receptor for VEGF-B$_{167}$, VEGF-C, VEGF-D or processed VEGF-B$_{186}$, wherein the protein has at least 90%, and preferably at least 95%, amino acid sequence identity with the NP-1-binding sequence of VEGF-B$_{167}$, VEGF-C, VEGF-D or processed VEGF-B$_{186}$, such that the protein, when provided to a cell expressing the cell surface receptor, is competent to interact specifically with the receptor and thereby substantially inhibits binding of VEGF-B$_{167}$, VEGF-C, VEGF-D or processed VEGF-B$_{186}$, respectively, to the receptor. The protein may desirably be an analog of VEGF-B$_{167}$, VEGF-C, VEGF-D or processed VEGF-B$_{186}$ obtained according to one of the methods described above, preferably an analog which does not induce cellular activities mediated by VEGF-B$_{167}$, VEGF-C, VEGF-D or processed VEGF-B$_{186}$.

The interacting domain in neuropilin or an isolated soluble NP binding domain or peptide of VEGF-B$_{167}$, VEGF$_{165}$, PlGF-2, VEGF-C or VEGF-D could be used as a soluble inhibitor of the full effects of any VEGF-B$_{167}$, VEGF$_{165}$, PlGF-2, VEGF-C or VEGF-D. The VEGF-B$_{167}$, VEGF$_{165}$, PlGF-2, VEGF-C or VEGF-D derived domain or peptide could also be anchored to the cell surface by various means, such as expression vector transformation, or linked domains with affinity to other cell surface molecules.

In accordance with a further aspect of the invention, pharmaceutical preparations are provided which comprise such growth factor/receptor complexes.

In yet another aspect of the invention a method is provided for treating a disease state characterized by overexpression of an NP-1 cell surface receptor, said method comprising administering to a patient suffering from said disease state an effective NP-1 receptor binding or receptor antagonizing amount of VEGF-B$_{167}$, VEGF-C, VEGF-D or processed VEGF-B$_{186}$ or an analog thereof obtained according to one of the methods described above.

NP-1 knockout and overexpression studies have shown interesting effects in the cardiovascular system, especially in the heart, where VEGF-B$_{167}$ is probably important. VEGF-B$_{167}$, VEGF-C, VEGF-D, processed VEGF-B$_{186}$ or derivatives thereof could also modulate the binding of the other ligands of NP-1, namely collapsin-1/semaphorinIII/D, semaphorin E and semaphorinIV, and in this way VEGF-B$_{167}$, VEGF-C, VEGF-D, processed VEGF-B$_{186}$ and/or derivatives thereof may affect the central nervous system.

Where the receptor protein comprises a polypeptide chain other than residues of NP-1 but which nevertheless exhibits a binding affinity for VEGF-B$_{167}$, VEGF-C, VEGF-D or processed VEGF-B$_{186}$, it should exhibit at least 80%, desirably at least 85%, preferably at least 90%, and especially preferably at least 95%, amino acid identity with the ligand-binding domain of NP-1. Similarly, useful analogs of VEGF-B$_{167}$, VEGF-C, VEGF-D or processed VEGF-B$_{186}$ should exhibit, respectively, at least 80%, preferably at least 85%, particularly preferably at least 90%, and especially preferably at least 95%, sequence identity to NP-1 binding domain of VEGF-B$_{167}$, VEGF-C, VEGF-D or processed VEGF-B$_{186}$.

On aspect of the invention is an isolated ligand-receptor complex comprising two molecules, one of the molecules defining the ligand and comprising the amino acid sequence encoded by exon 6B of VEGF-B$_{167}$ or a receptor-binding analog thereof, and a second of the molecules defining the receptor and being selected from the group consisting of a polypeptide chain comprising the amino acid sequence of NP-1, an extracellular domain thereof or a ligand-binding fragment thereof, a VEGF-B$_{167}$-binding or VEGF-C-binding receptor analog thereof having at least 90% amino acid identity with the ligand-binding fragment, and a polypeptide chain having binding affinity for VEGF-B$_{167}$ or VEGF-C and encoded by a nucleic acid that hybridizes under stringent conditions with a nucleic acid encoding the ligand-binding fragment.

A related aspect of the invention is an isolated ligand-receptor complex comprising two molecules, one of the molecules defining the ligand and being selected from the group consisting of VEGF-B$_{167}$, processed VEGF-B$_{186}$, VEGF-C, and VEGF-D and a second of the molecules defining the receptor and being selected from the group consisting of a polypeptide chain comprising the amino acid sequence of NP-1, an extracellular domain thereof or a ligand-binding fragment thereof, a VEGF-B$_{167}$-binding, processed VEGF-B$_{186}$-binding or VEGF-C-binding receptor analog thereof having at least 90% amino acid identity with the ligand-binding fragment, and a polypeptide chain having binding affinity for VEGF-B$_{167}$, processed VEGF-B$_{186}$ or VEGF-C and encoded by a nucleic acid that hybridizes under stringent conditions with a nucleic acid encoding the ligand-binding fragment. In one embodiment, the ligand is selected from the group consisting of VEGF-B$_{167}$, processed VEGF-B$_{186}$ and VEGF-C.

Yet a further embodiment of the invention is a soluble fusion protein comprising an immunoglobulin and a receptor moiety selected from the group consisting of a polypeptide chain comprising the amino acid sequence of NP-1, an extracellular domain thereof or a ligand-binding fragment thereof, a VEGF-B$_{167}$-binding, processed VEGF-B$_{186}$-binding or VEGF-C-binding receptor analog thereof having at least 90% amino acid identity with the ligand-binding fragment, and a polypeptide chain having binding affinity for VEGF-B$_{167}$, processed VEGF-B$_{186}$ or VEGF-C and encoded by a nucleic acid that hybridizes under stringent conditions with a nucleic acid encoding the ligand-binding fragment.

The invention further contemplates a modular assembly comprising at least a first protein domain and a second protein domain, the first domain comprising the amino acid sequence encoded by exon 6B of VEGF-B$_{167}$, and the second domain being selected from VEGF$_{165}$, VEGF-C, VEGF-D and processed VEGF-B$_{186}$.

A further aspect of the invention is a method of modulating binding and bioactivity of a growth factor selected from the group consisting of VEGF-B$_{167}$, VEGF-C, VEGF-D and processed VEGF-B$_{186}$, relative to living cells, the method comprising introducing into the cells a vector comprising a nucleotide sequence encoding a receptor sequence selected from the group consisting of a polypeptide chain comprising the amino acid sequence of NP-1, an extracellular domain thereof or a ligand-binding fragment thereof, a VEGF-B$_{167}$-binding, processed VEGF-B$_{186}$-binding or VEGF-C-binding receptor analog thereof having at least 90% amino acid identity with the ligand-binding fragment, and a polypeptide chain having binding affinity for VEGF-B$_{167}$, processed VEGF-B$_{186}$ or VEGF-C and encoded by a nucleic acid that hybridizes under stringent conditions with a nucleic acid the ligand-binding fragment.

In another aspect, the invention provides a method of inhibiting bioactivity of a growth factor selected from the group consisting of VEGF-B$_{167}$, VEGF-C, VEGF-D and processed VEGF-$B_{186}$, relative to living cells, the method comprising treating the cells with a polypeptide comprising the amino acid sequence encoded by exon 6B of VEGF-$B_{167}$ or a polypeptide comprising an NP-1 binding sequence encoded by exon 6A of VEGF-$B_{186}$. In a related aspect, the invention contemplates a method of inhibiting bioactivity of a growth factor selected from the group consisting of VEGF-$B_{167}$, VEGF-C, VEGF-D and processed VEGF-$B_{186}$, relative to living cells, the method comprising treating the cells with a polypeptide comprising the NP-1 binding epitope encoded by exon 6B of VEGF-$B_{167}$ or a polypeptide comprising an NP-1 binding sequence encoded by exon 6A of VEGF-$B_{186}$.

The invention also contemplates a method of modulating the responsiveness of cells to collapsin/semaphorin glycoproteins, comprising treating the cells with a substance selected from the group consisting of VEGF-$B_{167}$, VEGF-C, VEGF-D and processed VEGF-$B_{186}$. In a related aspect is provided a method of modulating the responsiveness of cells to collapsin/semaphorin glycoproteins, comprising treating the cells with a polypeptide comprising the NP-1 binding epitope encoded by exon 6B of VEGF-$B_{167}$ or a polypeptide comprising an NP-1 binding sequence encoded by exon 6A of VEGF-$B_{186}$. In one embodiment, the polypeptide comprises the amino acid sequence encoded by exon 6B of VEGF-$B_{167}$. In another embodiment, the polypeptide comprises an NP-1 binding sequence encoded by exon 6A of processed VEGF-$B_{186}$.

Also contemplated is a method of modulating the binding and bioactivity of a protein selected from the group consisting of VEGF-$B_{167}$, VEGF-C, VEGF-D and processed VEGF-$B_{186}$, relative to living cells, the method comprising introducing into cells a vector comprising a nucleotide sequence encoding a receptor sequence selected from the group consisting of a polypeptide chain comprising the amino acid sequence of NP-1, an extracellular domain thereof or a ligand-binding fragment thereof, a VEGF-$B_{167}$-binding, processed VEGF-$B_{186}$-binding or VEGF-C-binding receptor analog thereof having at least 90% amino acid identity with the ligand-binding fragment, and a polypeptide chain having binding affinity for VEGF-$B_{167}$, processed VEGF-$B_{186}$ or VEGF-C and encoded by a nucleic acid that hybridizes under stringent conditions with a nucleic acid encoding the ligand-binding fragment, whereby the cells are caused to express the receptor sequence.

Another aspect of the invention is a method of inhibiting growth or proliferation of tumor cells comprising the steps of treating the cells with: (a) a soluble protein selected from the group consisting of a polypeptide chain comprising the amino acid sequence of NP-1, an extracellular domain thereof or a hg and-binding fragment thereof, a VEGF-$B_{167}$-binding, processed VEGF-$B_{186}$-binding or VEGF-C-binding receptor analog thereof having at least 90% amino acid identity with the ligand-binding fragment, and a polypeptide chain having binding affinity for VEGF-$B_{167}$, processed VEGF-$B_{186}$ or VEGF-C and encoded by a nucleic acid that hybridizes under stringent conditions with a nucleic acid encoding the ligand-binding fragment; or (b) a polypeptide comprising the NP-1 binding epitope encoded by exon 6B of VEGF-$B_{167}$ or the NP-1 binding epitope encoded by exon 6A of processed VEGF-$B_{186}$. In one embodiment, the tumor cells are treated with soluble NP-1.

In a related embodiment, the tumor cells are treated with a polypeptide comprising the amino acid sequence encoded by exon 6B of VEGF-$B_{167}$. In a further embodiment, the polypeptide comprises an NP-1 binding sequence encoded by exon 6A of processed VEGF-$B_{186}$.

Also provided is an isolated binding partner having specific binding affinity for an epitope on a ligand-receptor complex, the complex comprising a protein selected from the group consisting of VEGF-$B_{167}$, VEGF-C, VEGF-D and processed VEGF-$B_{186}$ and analogs thereof in specific binding interaction with the ligand binding domain of a protein selected from the group consisting of a polypeptide chain comprising the amino acid sequence of NP-1, an extracellular domain thereof or a ligand-binding fragment thereof, a VEGF-$B_{167}$-binding, processed VEGF-$B_{186}$-binding or VEGF-C-binding receptor analog thereof having at least 90% amino acid identity with the ligand-binding fragment, and a polypeptide chain having binding affinity for VEGF-$B_{167}$, processed VEGF-$B_{186}$ or VEGF-C and encoded by a nucleic acid that hybridizes under stringent conditions with a nucleic acid encoding the ligand-binding fragment; the binding partner having substantially no binding affinity for uncomplexed VEGF-$B_{167}$, VEGF-C, VEGF-D, processed VEGF-$B_{186}$ or analog thereof. In one embodiment, the binding partner has substantially no binding affinity for an uncomplexed form of the protein or analog thereof. In a further embodiment, the binding partner is an antibody. In a related embodiment, the binding partner is a monoclonal antibody.

BRIEF DESCRIPTION OF THE DRAWINGS

The invention will be described in further detail hereinafter with reference to illustrative experiments, the results of which are illustrated in the accompanying drawings in which.

DETAILED DESCRIPTION OF ILLUSTRATIVE EXAMPLES

The invention will be described in further detail with reference to the following illustrative examples:

EXAMPLE 1

Cloning of the Soluble Neuropilin-1-Ig Fusion Construct

Figure 1:
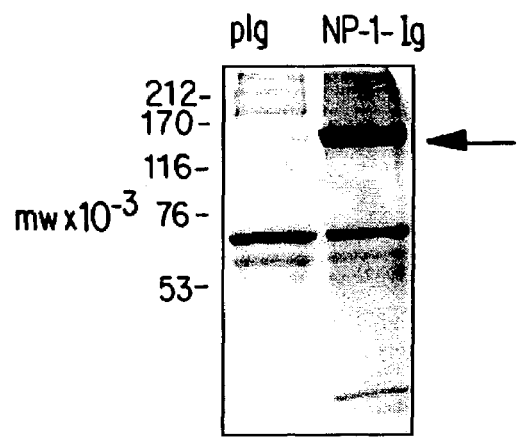
FIG. 1 shows an SDS-PAGE of pIg and NP-1-Ig from transfected 293T cells.

The extracellular domain of mouse NP-1 (248-2914 bp of mNeuropilin cDNA, Accession number D50086) was cloned into pIgplus (Ingenius). The 3' part (2738-2914 bp) of the extracellular domain was first ligated into pIgplus as an EcoR V-BamH I fragment and the 5' part (24R-2738 bp) then as an EcoR V fragment (the 5' EcoR V site is derived from pBluescript KSII vector). The sequence of the extracellular domain was thus cloned in frame with the pIgplus vector sequence encoding the human IgG Fc-part to allow fusion protein production, which could be precipitated by protein A sepharose from medium of transfected 293T cells, followed by SDS-PAGE and silver staining. Results are shown in FIG. 1. The NP-pIgplus or pIgplus was transfected into the cells and serum-free conditioned culture medium was collected between 24-32 hours after transfection. Proteins were detected by silver staining. As can be seen in FIG. 1, one approximately 135 kDa band was detected, whereas no such band was seen in the medium of cells transfected with the pIgplus vector only. The polypeptides migrating between 53-76 kD represent serum albumin. The low-molecular weight band at about 30 kD is believed to represent partial proteolysis of the $F_c$ tail.

EXAMPLE 2

Transfections, Immunoprecipitation and Soluble Receptor Binding

293-T cells were transfected with plasmids encoding the soluble receptor Ig-fusion proteins VEGFR-1-Ig (Olofsson et al., *Proc. Natl. Acad. Sci. USA*, 95:11716 (1998)), VEGFR-3-Ig or NP-1-Ig from Example 1 by using the calcium phosphate precipitation method. VEGFR-3-Ig was constructed by amplification of 7 Ig loops of R3 plus the Fc portion of human Ig placed in the vector pREP7.

The 293-T cells were incubated for 24 hours after transfection, washed with Dulbecco's Minimum Essential Medium (DMEM) containing 0.2% bovine serum albumin (BSA) and starved for 24-32 hours. Medium was collected and clarified by centrifugation and fusion proteins were precipitated by using protein A sepharose.

293-T or 293EBNA cells were similarly transfected with plasmids encoding hVEGF$_{165}$, mVEGF-B$_{167}$, mVEGF-B$_{186}$, hVEGF-C, hVEGF-D, PlGF-1 or PlGF-2, and the transfected cells were metabolically labeled 24 hours post transfection with 100 µCi/ml Pro-mix TML-$^{35}$S (Amersham) for 6 to 7 hours. 10 µg/ml heparin was added to the labeling medium to facilitate the release of the heparin sulphate-binding growth factors from the cell surface and pericellular matrix. Metabolically labeled media, with the exception of the medium used for VEGF transfection, were immunodepleted of endogenous VEGF by immunoprecipitating with VEGF antibody for two hours. Similar amounts of media containing the metabolically labeled growth factors were then used for immunoprecipitation or for receptor binding analysis. Growth factors were incubated for 3 hours at room temperature with receptor-Igs in binding buffer (phosphate buffered saline (PBS), 0.5% BSA, 0.2% Tween 20). The sepharose beads were then washed once with ice cold binding buffer and three times with PBS and analyzed by 15% SDS-PAGE.

Figure 2:
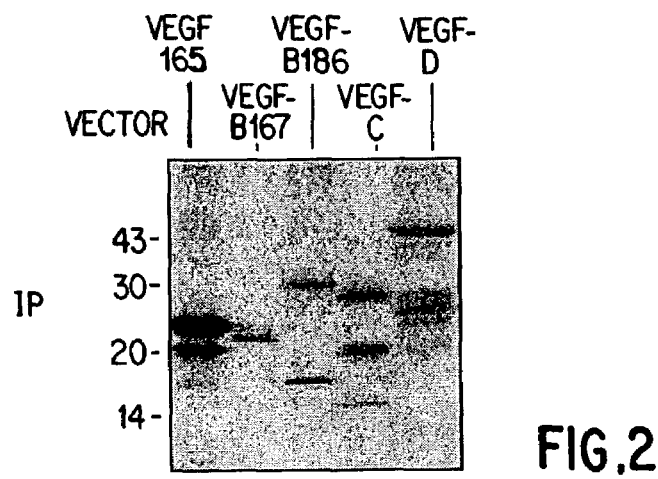
FIG. 2 shows affinity precipitation of metabolically labeled growth factors from conditioned media of transfected cells with specific antibodies.
Figure 3:
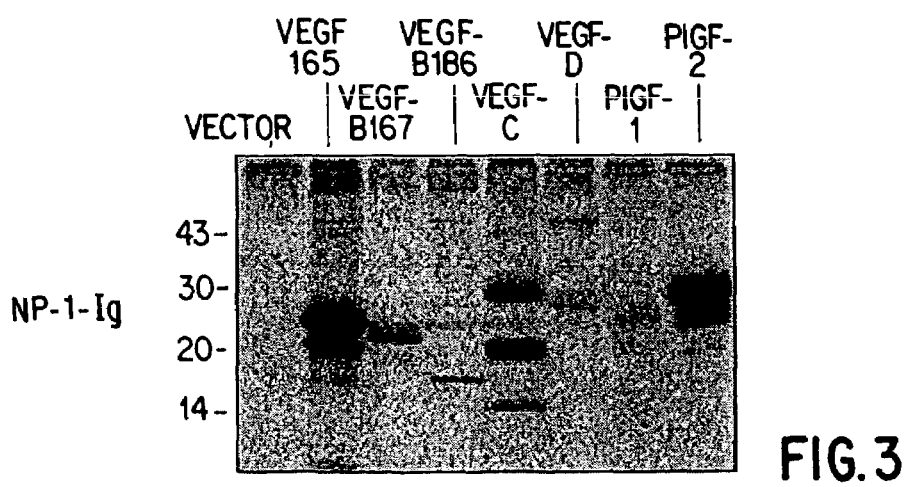
FIG. 3 shows affinity precipitation of metabolically labeled growth factors from conditioned media of transfected cells using receptor/immunoglobulin fusion proteins.
Figure 8:
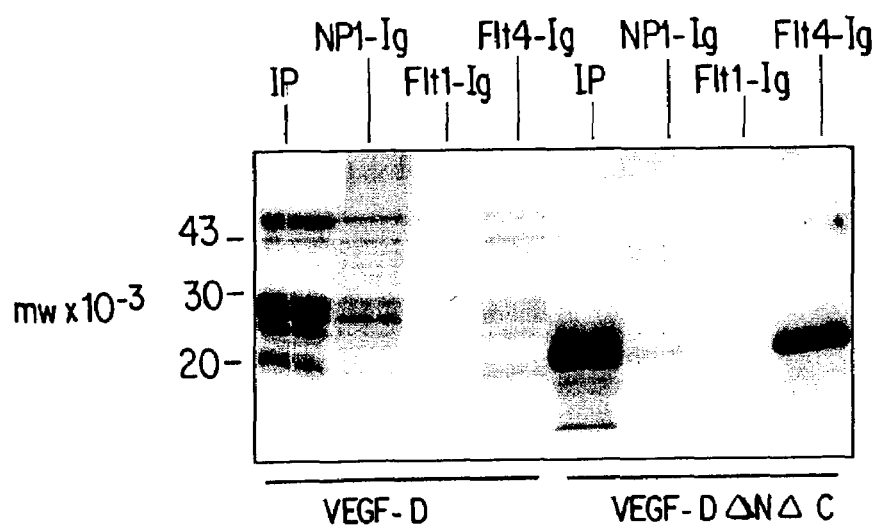
FIG. 8 shows binding of VEGF-D and VEGF-DΔNΔC to antibodies (IP), NP-1-Ig, Flt1-Ig and Flt4-Ig.

Immunoprecipitations were carried out using specific antibodies against VEGF$_{165}$, VEGF-B$_{167}$, VEGF-B$_{186}$, VEGF-C, VEGF-D and protein A sepharose. The results are shown in FIG. 2. Protein-A sepharose precipitation was also carried out using soluble NP-1-Ig protein coupled to protein A sepharose to precipitate metabolically labeled VEGF$_{165}$, VEGF-B$_{167}$, VEGF-B$_{186}$, VEGF-C, VEGF-D, PlGF-1 and PlGF-2 from conditioned media of transfected cells. Results of this are shown in FIG. 3. As can be seen from a comparison of FIG. 2 and FIG. 3, almost similar amounts of hVEGF$_{165}$, mVEGF-B$_{167}$, mVEGF-B$_{186}$ (processed form), hVEGF-C and PlGF-2 are precipitated by the soluble NP-1-Ig and by the specific antibodies. In contrast, no significant binding was detected between NP-1-Ig and hVEGF-D or PlGF-1. However, the results of FIG. 8 described below indicate that hVEGF-D can bind NP-1-Ig, although the interaction appears weak.

Figure 4:
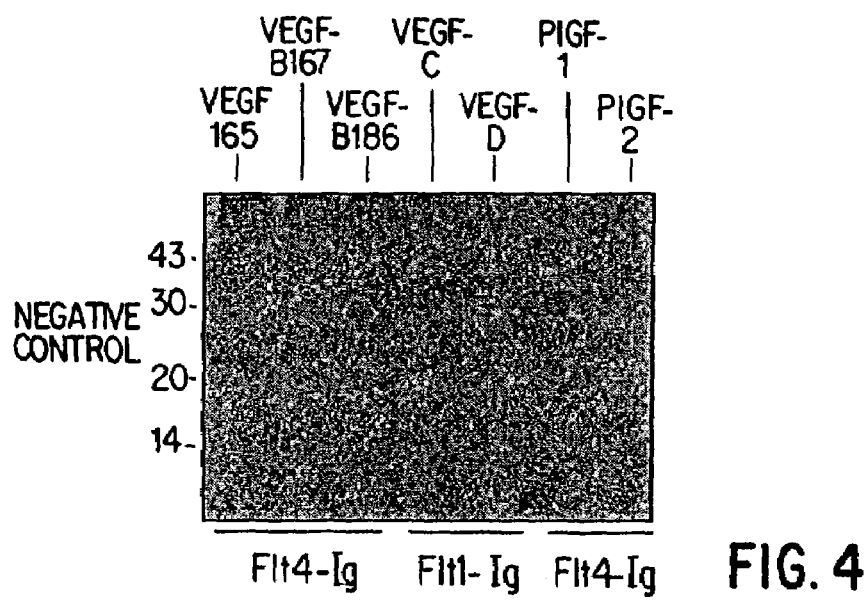
FIG. 4 shows affinity precipitation of metabolically labeled growth factors from conditioned media of transfected cells using Flt-1-Ig or Flt-4-Ig fusion proteins as negative controls.

As a negative control, affinity precipitation of metabolically labeled growth factors from conditioned media of transfected cells expressing VEGF$_{165}$, VEGF-B$_{167}$, VEGF-B$_{186}$, VEGF-C, VEGF-D, PlGF-1 and PlGF-2 was carried out using Flt-1-Ig or Flt-4-Ig. The results are shown in FIG. 4. The lack of binding of the indicated ligands to the indicted receptors was as expected.

EXAMPLE 3

Binding of VEGF Family Members to Specific Antibodies, NP-1, Flt-1 and Flt-4

The general procedure of Example 2 was repeated with conditioned media from cells expressing VEGF-B$_{167}$, VEGF-B$_{186}$, mVEGF-B$_{kEx1-5}$ (produced by expression of a construct containing exons 1-5 of murine VEGF-B), VEGF$_{165}$, VEGF-C, VEGF-CΔNΔC [a construct consisting of amino acids 102-225 of VEGF-C constructed as described in Joukov et al., *EMBO Journal*, 16:3898-911 (1997)], VEGF-D and VEGF-DΔNΔC [a construct consisting of amino acids 93-201 of VEGF-D constructed as described in Achen et al., *Proc. Natl. Acad. Sci. USA*, 95:548-53 (1998), respectively. The results are shown in FIGS. 5 through 8.

Figure 5:
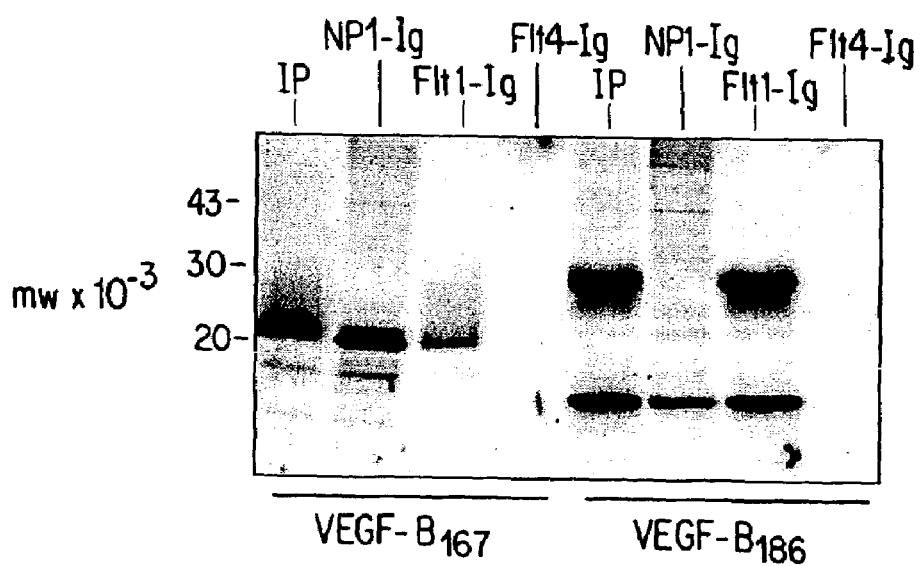
FIG. 5 shows binding of VEGF-$B_{167}$ and VEGF-$B_{186}$ to antibodies (IP), NP-1-Ig, Flt1-Ig and Flt4-Ig.
Figure 6:
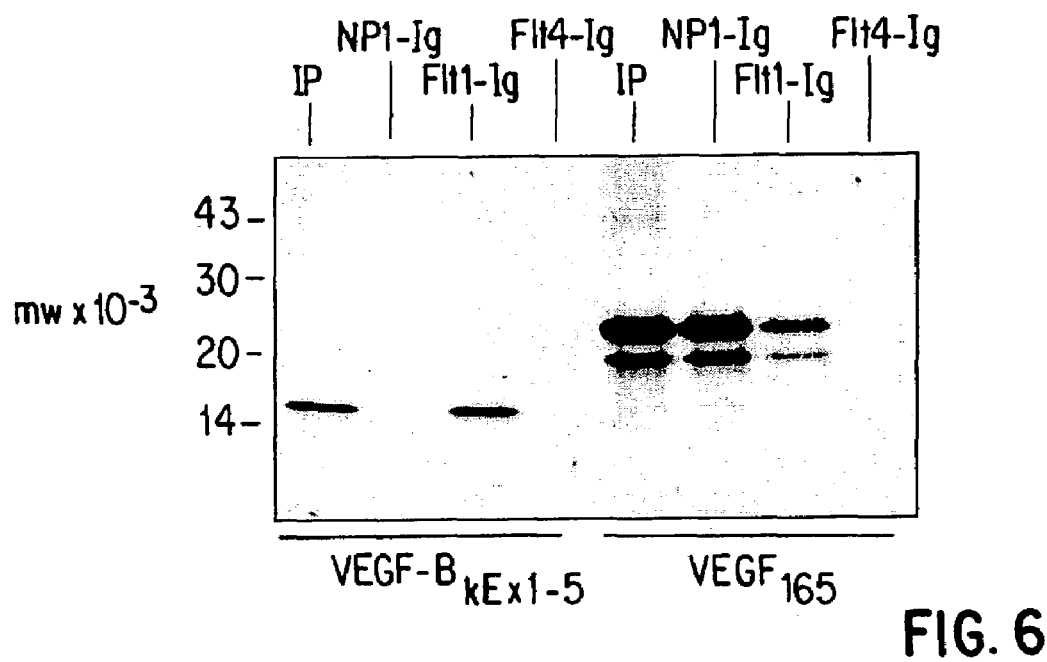
FIG. 6 shows binding of mVEGF-$B_{kEx1-5}$ and VEGF$_{165}$ to antibodies (IP), NP-1-Ig, Flt1-Ig and Flt4-Ig.
Figure 7:
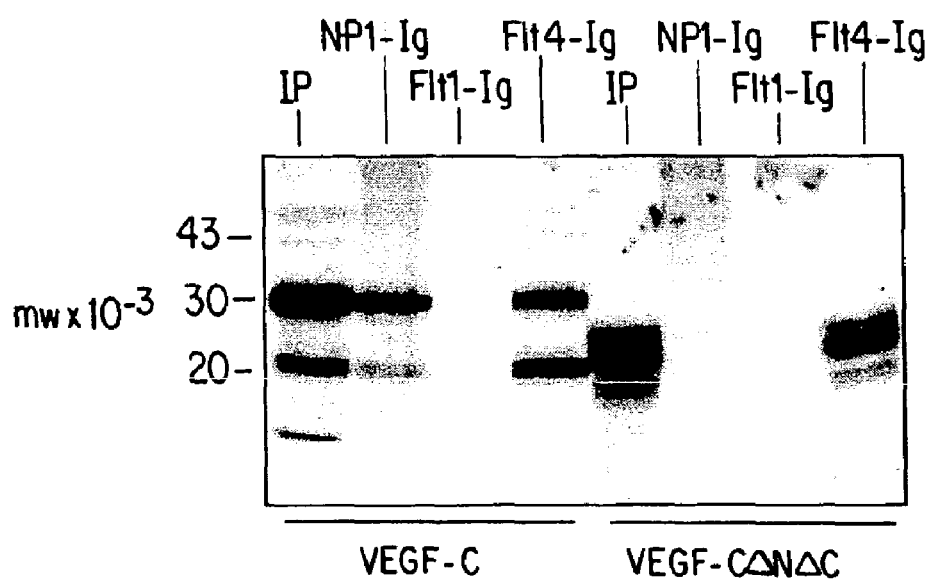
FIG. 7 shows binding of VEGF-C and VEGF-CΔNΔC to antibodies (IP), NP-1-Ig, Flt1-Ig and Flt4-Ig.

FIG. 5 shows assays for binding of ligands VEGF-B$_{167}$ and VEGF-B$_{186}$, and FIG. 6 shows assays for binding of ligands mVEGF-B$_{kEx1-5}$ and VEGF$_{165}$ to NP-1-Ig, Flt-1-Ig and Flt-4-Ig. In the Figure, the legend IP refers to immunoprecipitation and serves as a positive control using antibodies to the ligands. The antibody to VEGF-B$_{186}$ was a polyclonal antibody to the N-terminal peptide of VEGF-B described in WO 96/26736. This antibody also recognizes VEGF-B$_{167}$ and mVEGF-B$_{kEx1-5}$. The anti-VEGF$_{165}$ antibody was purchased from R&D Systems. In FIG. 6, the lack of binding of mVEGF-B$_{kEx1-5}$ to NP-1 can be seen. FIG. 5 shows that the VEGF-B$_{186}$ processed form (lower band) binds soluble NP-1, but the full length form (upper band) does not. Thus, the site of interaction is probably in the C-terminal region of processed VEGF-B$_{186}$ since mVEGF-B$_{kEx1-5}$ does not bind NP-1. It is most likely within exon 6A of VEGF-B$_{186}$ and is VEGF-CΔNΔC, and binding of VEGF-D and VEGF-DΔNΔC to NP-1-Ig, Flt1-Ig and Flt4-Ig. Binding of both full length VEGF-C and VEGF-D to Neuropilin-1 (NP-1) was detected. However, the truncated ΔNΔC-forms of VEGF-C and VEGF-D, which correspond to the mature forms of these growth factors, did not show any binding to NP-1.

EXAMPLE 4

Production and Purification of VEGF-$B_{167}$ GST-Fusion Protein and VEGF-$B_{186}$ GST-Fusion Protein Exon 6B covering amino acids 117-161 of mVEGF-$B_{167}$ was amplified by the polymerase chain reaction (PCR) using 5'-ACGTAGATCTAGCCCCAGGATCCTC-3' (SEQ ID NO:1) and 5'-ACGTG AATTCTCACCTACAGGT-TGCTGG-3' (SEQ ID NO:2) as primers. Amplified fragments were digested with the appropriate enzymes and ligated into the BamH I and EcoR I sites of the plasmid pGEX-2T (Pharmacia Biotech). The construct was verified by sequencing. *Escherichia coli* (*E. coli*) BL-21 were transformed with the construct and purified according to the manufacturer. Proteins were dialyzed in PBS overnight.

A GST fusion protein incorporating a polypeptide expression product of exon 6A and part of exon 6B of VEGF-$B_{186}$ (amino acids 116 through 163) also was produced analogously for use in later experiments.

EXAMPLE 5

Production and Purification of VEGF GST-Fusion Protein

Exon 7 of VEGF was amplified by the PCR using 5'-ATCGGGATCCCCCTGTGGGCCTTGC-3' (SEQ ID NO:3) and 5'-ACGTGAATTCTTAACATCTGCAAG-TACGTT-3' (SEQ ID NO:4) as primers.

Exon 7 of VEGF was amplified by the PCR using 5'-ATCGGGATCCCCCTGTGGGCCTTGC-3' (SEQ ID NO:3) and 5'-ACGTGAATTCTTAACATCTGCAAG-TACGTT-3' (SEQ ID NO:4) as primers. Amplified fragments were digested with the appropriate enzymes and ligated into the BamHI and EcoR I sites of pGEX-2T (Pharmacia Biotech). The construct was verified by sequencing. *E. coli* BL-21 were transformed with the construct and purified according to the manufacturer. Proteins were dialyzed in PBS overnight.

EXAMPLE 6

Affinity Chromatography with GST-VEGF-$B_{167}$ Exon 6B.

Figure 9:
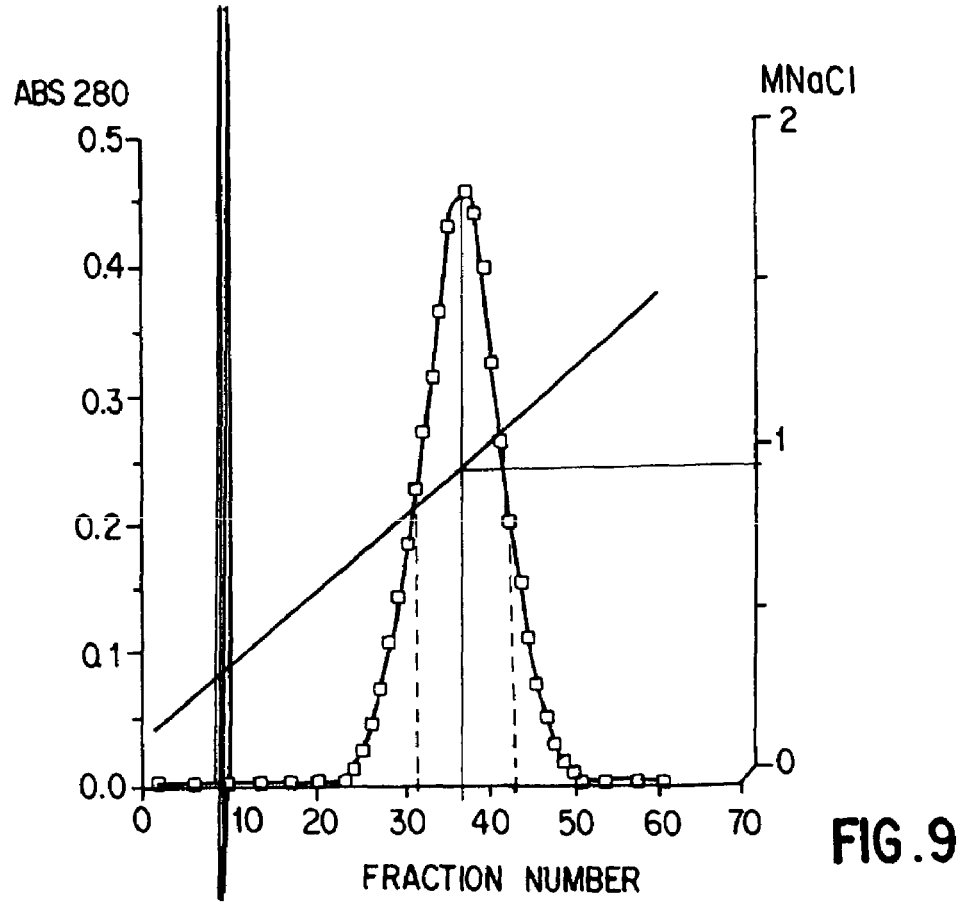
FIG. 9 shows affinity chromatography of GST-VEGF-$B_{167}$.
Figure 10:
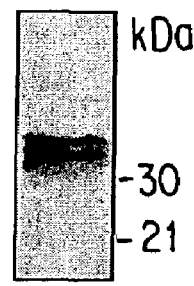
FIG. 10 shows a silver-stained SDS-PAGE with eluted material from FIG. 9.

Glutathione agarose purified GST-VEGF-$B_{167}$ exon 6B was applied to a Hi-trap heparin sepharose affinity column (5 ml) and washed extensively, and then eluted from the column by a linear salt gradient of 0.15-1.5 M NaCl in 20 mM Na-phosphate buffer, pH 7.2. The results are displayed in FIG. 9. The affinity chromatography shows that the exon 6B encoded sequence of VEGF-$B_{167}$ (GST-VEGF-$B_{167}$) interacts with heparin and the majority of the protein can be eluted with 0.8 M NaCl. FIG. 10 shows a silver stained SDS-PAGE of the eluted material.

EXAMPLE 7

Binding to Soluble Receptors and Competition with GST Fusions

293-T cells are transfected with plasmids encoding soluble Ig-fusion receptors VEGFR-1 and NP-1. Media are then collected from transfected cells after being starved in DMEM containing 0.2% BSA for 24 hours post-transfection. The fusion proteins are precipitated using protein A-sepharose. The ligands are produced by transfection of 293-T cells with hVEGF$_{165}$pSG5, mVEGF-$B_{167}$pSG5, mVEGF-$B_{186}$pSG5 and mVEGF-$B_{kEx1-5}$pSG5 (Olofsson et al., *Proc. Natl. Acad. Sci. USA*, 95:11716 (1998)) and the cells are metabolically labeled with 100 µCi/ml, using Pro-mix TML-35 S (Amersham) for 6-7 hours in the presence of 10 mg/ml heparin. Metabolically labeled media, except for the medium for the hVEGF$_{165}$ transfections, are immunodepleted of endogenous VEGF and possible VEGF heterodimers using VEGF antibodies for two hours. Growth factors and an equal amount of media from mock-transfected cells are bound to soluble receptor-Ig fusions for three hours at 4° C. and washed with 1% Triton-X100 in PBS three times and PBS once and analyzed under reducing conditions by 15% SDS-PAGE. For competition 25 mg of each GST fusion protein prepared in Examples 4 and 5 above, and GST alone are incubated for 30 minutes with the metabolic medium before the receptor pull-down and analyzed as above.

EXAMPLE 8

Competition of $^{125}$I-hVEGF$_{165}$ Binding to NP-1 by GST-VEGF-$B_{167}$ and GST-VEGF-$B_{186}$ on Cell Bound Receptors Human recombinant VEGF$_{165}$ was radiolabeled with $^{125}$I-reagent to a specific activity of 2.5×10$^5$ cpm/ng. Confluent porcine aortic endothelial (PAE) cells, PAE-NP-1 cells and PAE-NP-1-VEGFR-1 cells seeded in 24 well plates were washed once with ice cold binding buffer (F12, 0.5 mg/ml BSA, 20 mM Hepes pH 7.4), and 1 ng/ml of labeled VEGF with or without increasing amounts of rhVEGF$_{165}$, rhVEGF$_{121}$ (R&D Systems), GST, GST-VEGF (See Example 5), GST-VEGF-$B_{167}$ (See Example 4) and GST-VEGF-$B_{186}$ (produced analogously) was added in binding buffer. PAE-NP-1 cells expressing NP-1 were obtained from Soker et al., *Cell*, 92:735-45 (1998). The PAE-NP-1 cells were then transfected with a construct containing the full length human VEGF receptor 1 in pcDNA 3.1 vector, and the resulting transfectants were selected with zeocin to obtain PAE-NP-1-VEGFR-1 cells. Binding was performed for two hours at 4 degrees C., after which the cells were washed four times with ice cold binding buffer (F12, 0.5 mg/ml bovine serum albumin (BSA); 20 mM Hepes pH 7.4) containing 5 µg of heparin per ml, and once with ice cold PBS, and then lyzed in 0.5 M NaOH. Cell lysate radioactivity was counted with a gamma counter.

Figure 11:
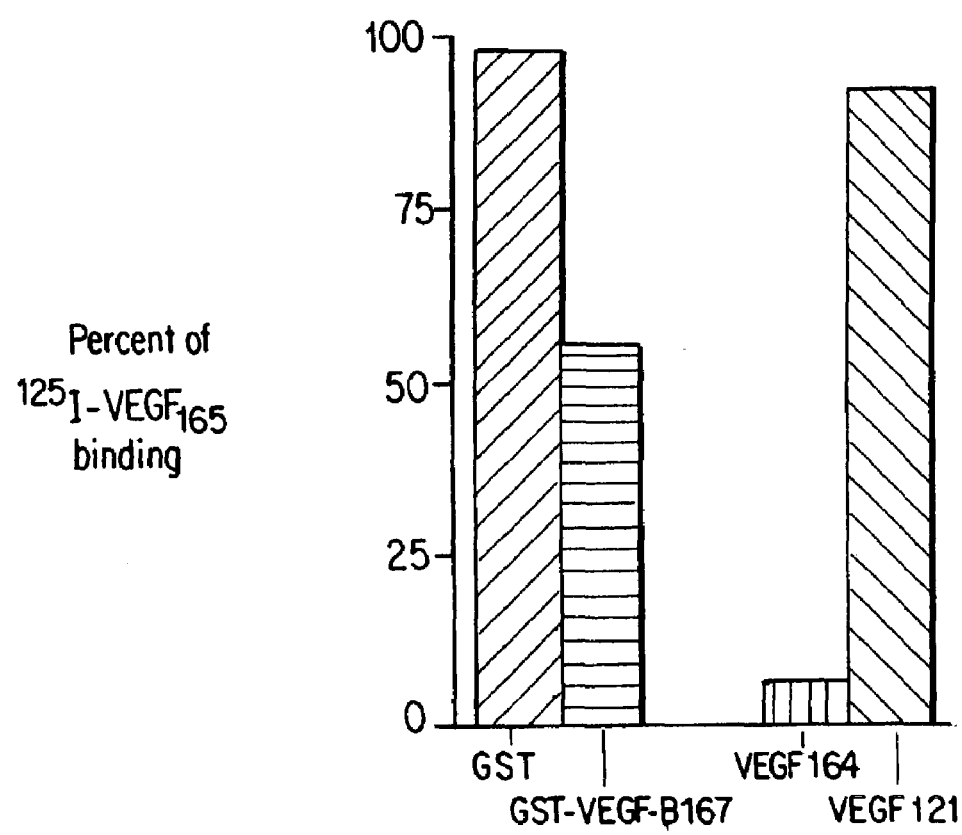
FIG. 11 is a bar graph showing results of competitive binding tests of GST-mVEGF-$B_{167}$ (exon 6B) for VEGF binding to PAE-NP-1 cells.

Results of the competition of $^{125}$I-hVEGF$_{165}$ binding to NP-1 by GST-VEGF-$B_{167}$ (exon 6B) are shown in FIG. 11. 1 ng/ml $^{125}$I-hVEGF$_{165}$ and 20 µg of the GST fusion per ml were used. The GST-VEGF-$B_{167}$ has low affinity, and as can be seen from FIG. 11, about 50% competition was accomplished. Negative controls used were GST alone and VEGF$_{121}$, neither of which competes. As a positive control, mVEGF$_{164}$ was used, which does compete.

EXAMPLE 9

Cross-Linking of GST-VEGF$_{167}$ and GST-VEGF-B$_{186}$ to NP-1 Expressing Cells GST fusions and VEGF-B$_{167}$ and VEGF-B$_{186}$ are radiolabeled as above and cross-linked as described in Cao et al., *J. Biol. Chem.*, 271:3154 (1996) to transfected cells expressing NP-1 and coexpressing NP-1 and VEGFR-1 (Example 8) seeded in 6 well plates using 10 ng labeled protein and disuccinimidyl suberate (DSS) cross-linker (Pierce). The cross-linked proteins are resolved by 6% SDS-PAGE under reducing conditions. Excess (1 μg) rhVEGF$_{165}$ is added as a competitor.

EXAMPLE 10

Direct Interaction Between VEGFR-1 and NP-1

Soluble myc-tagged NP-1 and PAE-Flt1 cells or NIH-VEGFR-1 cells (Sawano et al., *Cell Growth and Differentiation*, 7:213-21 (1996)) are used to test the interaction between VEGFR-1 and NP-1. The myc-tagged NP-1 was produced by attaching a C-terminal myc tag on the extracellular domain of NP-1. Soluble NP-1 (sNP-1) is cross-linked to cells in the absence or presence of ligand and cross-linked material are immunoprecipitated with a monoclonal anti-myc antibody. The anti-myc antibody was obtained from Berkeley Antibody Company (Babco). The complex is resolved by 6% SDS-PAGE, transferred to nitrocellulose and probed with Flt1 antibody (Santa Cruz).

Figure 12:
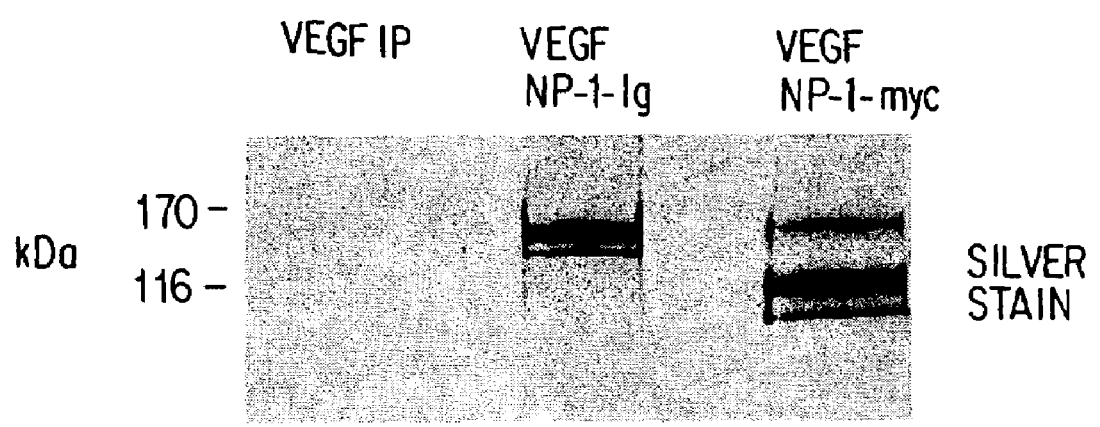
FIG. 12 shows the results of binding experiments with NP-1-Ig and NP-1-myc antibodies with VEGF.
Figure 13A:
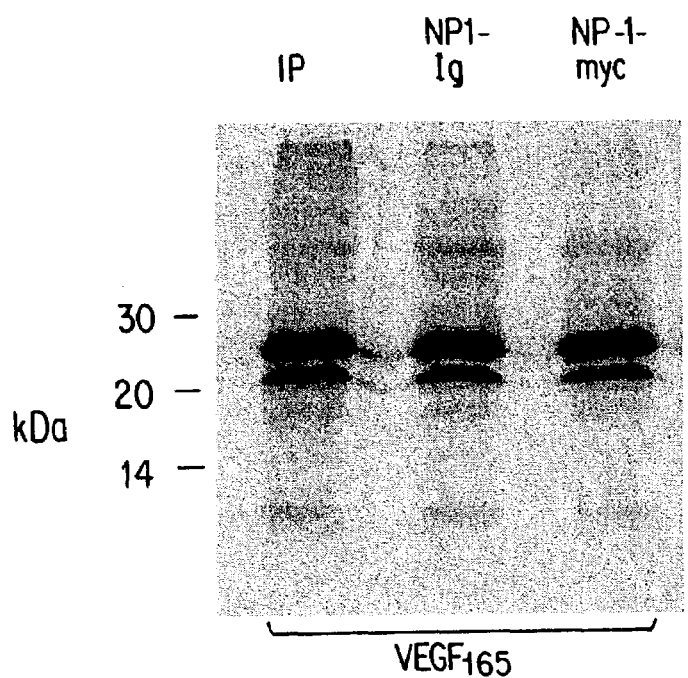
FIGS. 13(a), (b) and (c) show, respectively, the results of binding experiments with VEGF, VEGF-$B_{167}$ and VEGF-$B_{186}$ with NP-1-Ig and NP-1-myc antibodies.
Figure 13B:
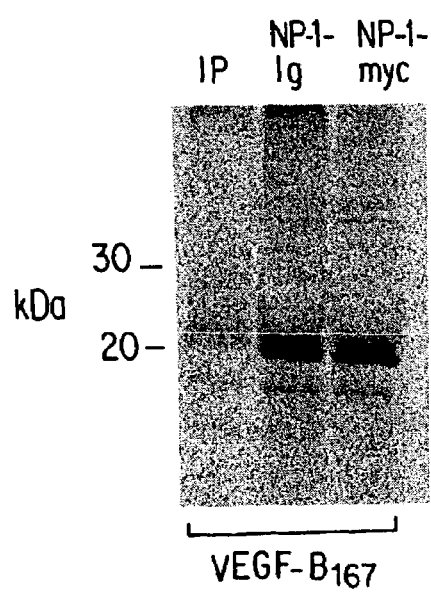
Figure 13C:
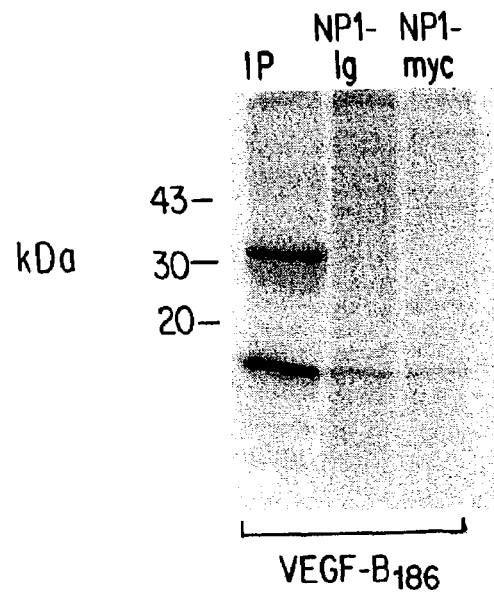

The results are shown in FIGS. 12 and 13. In FIG. 12 is shown that equal amounts of NP-1-Ig and NP-1-myc are used in the binding experiments. In FIG. 13(*a*), (*b*) and (*c*) are shown the binding results of VEGF, VEGF-B$_{167}$ and VEGF-B$_{186}$. Dimeric NP-1-Ig and monomeric NP-1-myc bind at least VEGF and VEGF-B$_{167}$ at similar strength. The binding of VEGF-B$_{186}$ appears weaker.

EXAMPLE 11

Testing NP-1 and/or NP-1 Mimetic Molecules

Excess soluble NP-1 (sNP-1) can block VEGF, VEGF-B, VEGF-C and VEGF-D signaling by preventing interaction with the RTK on endothelial cells and on receptor expressing cells in a manner similar to sFlt1 (Goldman et al. 1998). In vitro tests are performed by stimulating receptors with the test ligand in the presence of excess NP-1. Results are quantified by measuring autophosphorylation either in an in vitro kinase assay or an anti-phosphotyrosine Western blot.

EXAMPLE 12

Direction of Ligands to Different Cell Types

Ligands of the VEGF family which bind to the NP-1 receptor can be directed to different types of cells by transforming the cells in vivo with viral vectors containing NP-1 DNA such that the cells express the NP-1 receptor.

EXAMPLE 13

Low Stringency Hybridization with NP-1 and NP-2 for Tissue Specific Homologs

Homologs of the NP-1 receptor can be tested for ligand binding of members of the VEGF family and fibroblast growth factor family by screening binding tests under low stringency conditions as described above.

EXAMPLE 14

Direct Binding of Soluble NP-1 to VEGF-B$_{167}$

Figure 14:
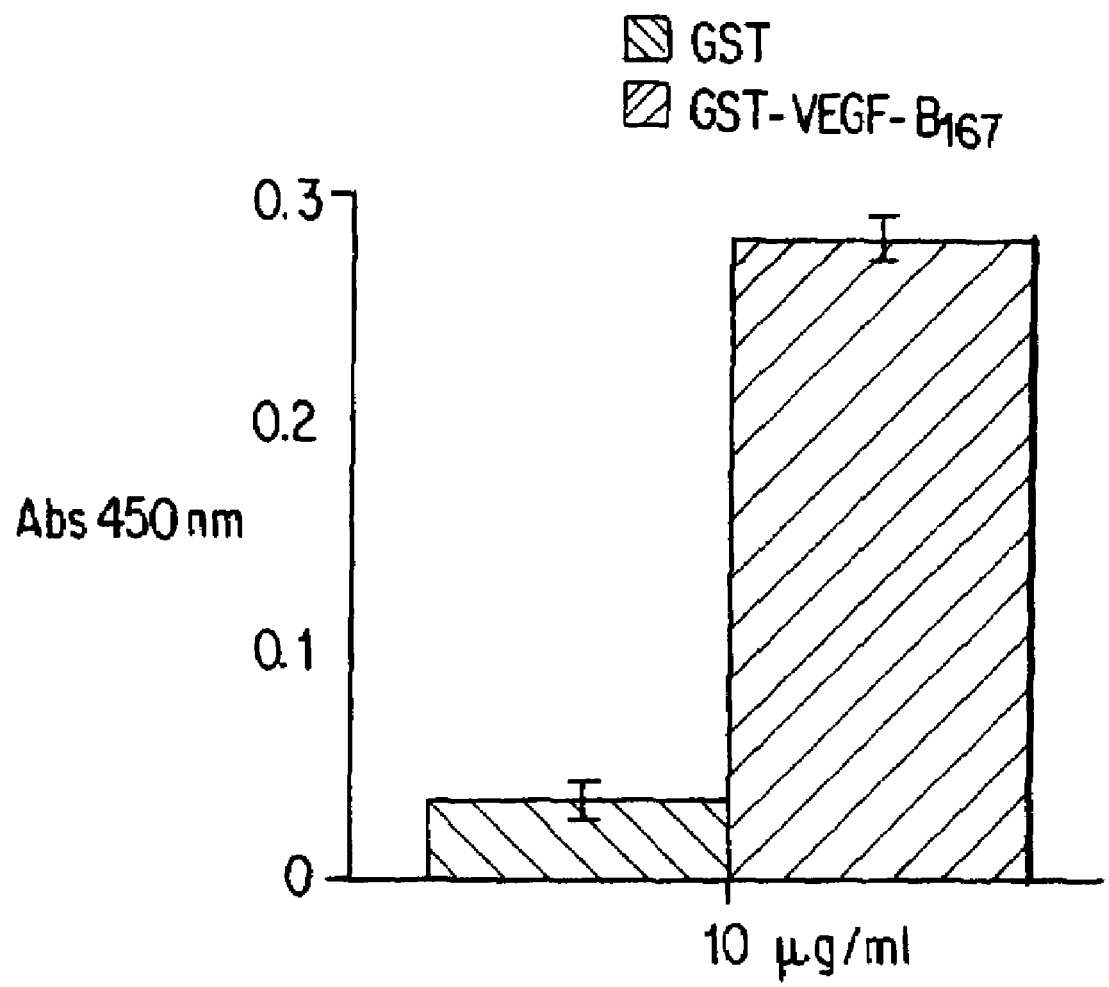
FIG. 14 shows the results of the direct binding experiments with VEGF-$B_{167}$ and NP-1-Ig.

To further assess the interactions between NP-1 and VEGF-B$_{167}$, VEGF-B$_{167}$ was tested for its capacity to directly bind soluble NP-1-Ig fusion proteins. Purified GST or GST-VEGF-B$_{167}$ was coated onto ELISA plates for 90 minutes at room temperature. The protein solution was removed and the coated wells were blocked with 5% (BSA) in PBS for 30 minutes. Plates were washed three times with 0.5 mg/ml BSA in PBS and incubated with soluble NP-1-Ig at a concentration of 1 μg/ml. The binding was allowed for two hours at room temperature. The plates were washed three times as above before addition of anti-human Ig conjugated with horse radish peroxidase (HRP). The anti-human Ig antibody was left for 40 minutes on the wells after which the plates were washed as above, with one additional wash with PBS and then 100 μl of the substrate 1,2-phenylene-diamine dihydrochloride (ODP) was added according to supplier (DAKO). The reaction was stopped by the addition of 100 μl of 0.5 M H$_2$SO$_4$. The absorbance was read at 450 nm. Results are shown in FIG. 14. Flt-4-Ig was used as a negative control, and it does not bind to GST or GST-VEGF-B$_{167}$ (results not shown).

Usefulness

The interaction between members of the VEGF family of growth factors, such as VEGF-B$_{167}$, VEGF-C, VEGF-D or processed VEGF-B$_{186}$, and the Neuropilin-1 receptor may be used to potentiate the action of the ligand by transforming cells where the growth factor activity is to be potentiated with, for example, viral vectors bearing NP-1 DNA such that the cells express excess NP-1 receptors.

The formation of complexes between NP-1 receptors and VEGF-B$_{167}$, VEGF-C, VEGF-D or processed VEGF-B$_{186}$ or analogs thereof may be used as a treatment for disease states characterized by overexpression of the NP-1 receptor by administering to a patient suffering from such a disease state an effective NP-1 receptor binding or receptor antagonizing amount of VEGF-B$_{167}$, VEGF-C, VEGF-D or processed VEGF-B$_{186}$ or an analog thereof. The formation of complexes between NP-1 and VEGF-B$_{167}$, VEGF-C, VEGF-D or processed VEGF-B$_{186}$ or an analog thereof may also be useful in treating states characterized by underexpression of an NP-1 receptor. Such states may include normal adult endothelium or states which require increased blood vessel formation. The amount to be administered in a given case will depend on the characteristics of the patient and the nature of the disease state and can be determined by a person skilled in the art by routine experimentation.

Certain isoforms of VEGF-B may be involved in promoting endothelial cell growth migration and stimulation and tube formation. Increase by transfection or transduction of neuropilin expression in cells in vitro or in vivo may make the cells more responsive to the isoforms. Expression of neuropilin by cells adjacent to those expressing a particular RTK could also modulate the effective concentrations and signals by the RTK.

Transfection or transduction of nucleic acid encoding neuropilin could be performed to increased expression in cells in vitro and in vivo. Expression in cells not expressing neuropilin, [e.g. hematopoietic cells, see Soker et al., Cell, 92:735-745 (1998)] should make them more responsive to VEGF-$B_{167}$ but not to the unprocessed (i.e., full length) form of VEGF-$B_{186}$.

Heparin should modulate neuropilin binding as well, and a basic, heparin binding peptide of VEGF-$B_{167}$ could modulate it independently of direct NP-1 interaction. VEGF-C does not bind heparin, so VEGF-C would not be modulated.

The interacting domain in neuropilin or an isolated soluble NP binding domain or peptide of VEGF-$B_{167}$, VEGF$_{165}$, PlGF-2, VEGF-C, VEGF-D or the processed form of VEGF-$B_{186}$ could be used as a soluble inhibitor of the full effects of any of VEGF-$B_{167}$, VEGF$_{165}$, PlGF-2, VEGF-C, VEGF-D or the processed form of VEGF-$B_{186}$. The VEGF-$B_{167}$, VEGF$_{165}$, VEGF-C, VEGF-D, PlGF-2 or processed form of VEGF-$B_{186}$ derived domain or peptide could also be anchored to the cell surface by various means, such as expression vector transformation, or linked domains with affinity to other cell surface molecules.

NP-1 may be associated with tumor cells. Abolishing interaction of VEGF-$B_{167}$, VEGF-C, VEGF-D, PlGF-2 and/or the processed form of VEGF-$B_{186}$ with NP-1 could alleviate biological activity in cancer. It is also possible that one or more of these growth factors signals without Flt-1 by an as yet unknown mechanism, and the mechanism occurs in tumor cells. Abolished interaction would modulate this signaling mechanism.

NP-1 knockout and overexpression studies have shown interesting effects on the cardiovascular system, especially in the heart where VEGF-$B_{167}$ probably is important. VEGF-$B_{167}$ could also modulate the binding of the other ligands of NP-1, namely collapsin-1/semaphorinIII/D, semaphorin E and semaphorinIV$_1$ and thereby affect the central nervous system.

VEGF-$B_{167}$, VEGF-C, VEGF-D or processed VEGF-$B_{186}$ or an analog thereof may suitably be administered intravenously or by means of a targeted delivery system analogous to the systems heretofore used for targeted delivery of VEGF or FGF. Examples of such systems include use of DNA in the form of a plasmid (Isner et al., Lancet, 348:370 (1996)) or use of a recombinant adenovirus (Giordano et al., Nature Medicine, 2:534-39 (1996)). VEGF-$B_{167}$, VEGF-C, VEGF-D or processed VEGF-$B_{186}$ could also be provided in protein form by techniques analogous to those described for VEGF (Bauters et al., The American Physiological Society, pp H1263-271 (1994); Asahara et al., Circulation, 91:2793 (1995)) or through use of a defective herpes virus (Mesri et al., Circulation Research, 76:161 (1995)). Small molecule analogs of VEGF-$B_{167}$, VEGF-C, VEGF-D or processed VEGF-$B_{186}$ could be administered orally. Other standard delivery modes, such as sub-cutaneous, intradermal, intramuscular, intraperitoneal or intravenous injection, could also be used.

Complexes of NP-1 receptor or portions thereof with VEGF-$B_{167}$, VEGF-C, VEGF-D or processed VEGF-$B_{186}$ protein also can be used to produce antibodies. The antibodies may be either polyclonal antibodies or monoclonal antibodies. In general, conventional antibody production techniques may be used to produce antibodies to NP-1/growth factor complexes. For example, specific monoclonal antibodies may be produced via immunization of fusion proteins obtained by recombinant DNA expression. Both chimeric and humanized antibodies and antibody fragments to the VEGF-$B_{167}$/receptor complex are expressly contemplated to be within the scope of the invention. Labeled monoclonal antibodies, in particular, should be useful in screening for medical conditions characterized by overexpression or underexpression of the NP-1 receptor. Examples of such conditions include endothelial cell tumors of blood and lymphatic vessels.

In a diagnostic/prognostic device, the antibody as described above, the growth factor or the receptor is labeled, and one of the remaining two which is not labeled is substrate-bound, such that the antibody-growth factor/receptor complex can be established by determining the amount of label attached to the substrate following binding between the antibody and the growth factor/receptor complex. A conventional ELISA kit is an example of this diagnostic/prognostic device.

Labeling may be direct or indirect, covalent or non-covalent. Either the antibody, the growth factor or the receptor may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels are a radioactive atom or group, such as $^{125}I$ or $^{32}p$ Examples of non-radioactive labels are enzyme, such as horseradish peroxidase, or fluorimetric labels, such as fluorescein-5-isothiocyanate (FITC).

A diagnostic/prognostic kit may also comprise use of the PCR to determine expression of NP-1 and/or the respective growth factor.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A fusion protein comprising at least a first protein domain and a second protein domain, the first domain comprising the amino acid sequence encoded by exon 6B of VEGF-B$_{167}$, and the second domain being selected from VEGF$_{165}$, VEGF-C, VEGF-D and processed VEGF-B$_{186}$.

2. The fusion protein of claim 1 wherein the second protein domain is VEGF$_{165}$.

3. The fusion protein of claim 1 wherein the second protein domain is VEGF-C.

4. The fusion protein of claim 1 wherein the second protein domain is VEGF-D.

5. The fusion protein of claim 1 wherein the second protein domain is processed VEGF-B$_{186}$.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Homo sapiens

<400> SEQUENCE: 1
acgtagatct agccccagga tcctc                                          25

```
<210> SEQ ID NO 2
<211> LENGTH: 28
<212> TYPE: DNA
<213> ORGANISM: Homo sapiens

<400> SEQUENCE: 2
acgtgaattc tcacctacag gttgctgg                                        28

<210> SEQ ID NO 3
<211> LENGTH: 25
<212> TYPE: DNA
<213> ORGANISM: Homo sapiens

<400> SEQUENCE: 3
atcgggatcc ccctgtgggc cttgc                                           25

<210> SEQ ID NO 4
<211> LENGTH: 30
<212> TYPE: DNA
<213> ORGANISM: Homo sapiens

<400> SEQUENCE: 4
acgtgaattc ttaacatctg caagtacgtt                                      30
```